United States Patent [19]

Kurahashi et al.

[11] Patent Number: 4,623,377
[45] Date of Patent: Nov. 18, 1986

[54] 1,2,3,4-TETRAHYDROQUINOLIN-1-YLCARBONYLIMIDAZOLES AND HERBICIDAL USE THEREOF

[75] Inventors: Yoshio Kurahashi, Hachioji; Kozo Shiokawa, Kawasaki; Toshio Goto, Machida; Shinzo Kagabu, Hachioji; Atsumi Kamochi, Hino; Koichi Moriya, Hachioji; Hidenori Hayakawa, Musashino, all of Japan

[73] Assignee: Nihon Tokushu Noyaku Seizo K.K., Tokyo, Japan

[21] Appl. No.: 725,073

[22] Filed: Apr. 19, 1985

[30] Foreign Application Priority Data

Apr. 20, 1984 [JP] Japan .................................. 59-78719

[51] Int. Cl.$^4$ .................. C07D 401/06; A01N 43/38; A01N 43/50
[52] U.S. Cl. ........................................ 71/92; 546/165
[58] Field of Search ............................ 546/165; 71/92

[56] References Cited

U.S. PATENT DOCUMENTS 3,308,131  3/1967  McKusick ............................ 260/294
4,497,651  2/1985  Hagen et al. ........................ 546/180

FOREIGN PATENT DOCUMENTS 762408  2/1970  Belgium .
0023306  2/1981  European Pat. Off. .
1052308  12/1966  United Kingdom .
1154722  6/1969  United Kingdom .

*Primary Examiner*—Glennon H. Hollrah
*Assistant Examiner*—W. B. Springer
*Attorney, Agent, or Firm*—Sprung Horn Kramer & Woods

[57] ABSTRACT

Tetrahydroquinolin-1-ylcarbonylimidazoles of the formula

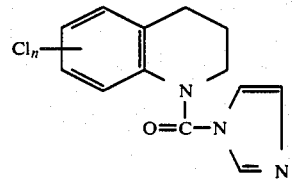

in which
n is 0, 1, 2 or 3, which possess herbicidal and fungicidal activity. The corresponding intermediates of the formula

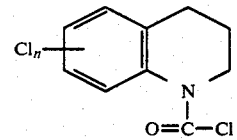

are also new.

7 Claims, No Drawings

1,2,3,4-TETRAHYDROQUINOLIN-1-YLCARBONYLIMIDAZOLES AND HERBICIDAL USE THEREOF

DETAILED DESCRIPTION OF THE INVENTION

This invention relates to tetrahydroquinolin-1-yl-carbonylimidazole derivatives, intermediates thereof, processes for production thereof, and herbicides or agricultural and horticultural fungicides.

More specifically, this invention relates to tetrahydroquinolin-1-ylcarbonylimidazole derivatives represented by the following general formula (I):

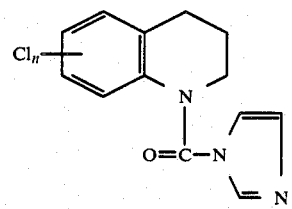

(I)

wherein
n represents 0, 1, 2 or 3.

The compounds of general formula (I) can be produced, for example, by the following processes to which the invention also pertains:

Process (i)

A process for producing the compounds of general formula (I), which comprises reacting a compound represented by the general formula

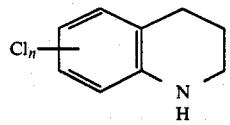

(II)

wherein
n is as defined
with a compound represented by the following formula:

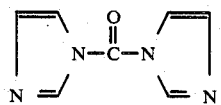

Process (ii)

A process for producing the compounds of general formula (I), which comprises reacting a compound represented by the general formula

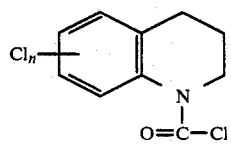

(III)

wherein
n is as defined, with imidazole represented by the formula:

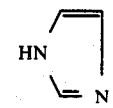

This invention also pertains to a herbicide and an agricultural and horticultural fungicide comprising the compound of general formula (I) as an active ingredient.

The invention further relates to the compound of general formula (III) which is an intermediate used in the process for producing the compound of general formula (I).

The compound of general formula (III) can be produced, for example, by the following process to which the invention also pertains.

Process (iii)

A process for producing the compound of general formula (III), which comprises reacting the compound of general formula (II) with phosgene or trichloromethyl chloroformate.

U.S. Pat. No. 3,308,131 known before the filing date of the present application gives a description about tertiary carbamyltriazoles represented by a general formula which cannot encompass the compounds of the invention represented by formula (I), and states that these compounds have insecticidal activity. The U.S. Patent specifically discloses a compound of the following formula.

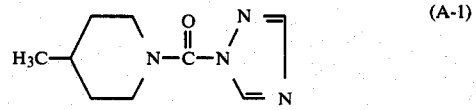

(A-1)

Japanese Patent Publication No. 17748/1968 gives a description about 2,4,5-tribromoimidazole derivatives represented by a general formula which cannot embrace the compounds of the invention represented by formula (I), and states that these derivatives have insecticidal and herbicidal activities. The Japanese patent document specifically discloses a compound represented by the following formula.

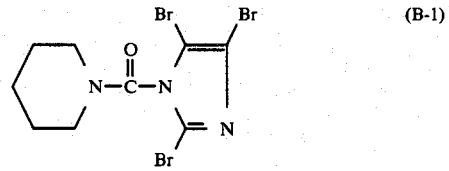

(B-1)

The present invention made extensive investigations in order to create novel biologically active compounds, and have now succeeded in synthesizing the tetrahydroquinolin-1-ylcarbonylimidazole derivatives. We have found that these compounds have biological activities, for example herbicidal activity and fungicidal activity, and selectivity for useage crops.

The investigations of the present inventors have shown that the compounds of general formula (I) in accordance with this invention are novel compounds not described in any literature references before the filing of the present application, and can be easily produced as will be described in detail hereinbelow. It has also been found that as will be apparent from the following description, the compounds of formula (I) in accordance with this invention have herbicidal activity, particularly an excellent controlling action on paddy weeds, and at the same time, show excellent affinity for rice plants in aquatic paddy.

The inventors have further discovered that the compounds of the invention further possess controlling activity on plant diseases and show an excellent controlling action on, for example, brown leaf spot of rice (*Ophiobolus miyabeanus*), black rot of cruciferous plants (*Alternaria brassicae*), alternaria leaf spot of apple (*Alternaria mali*), and phytophthora blight of various plants (*Phytophthora infestans*).

It has been found in accordance with this invention that the above biological characteristics of the compounds of formula (I) in accordance with this invention are associated with their chemical characteristics, that is, their unique chemical structure. Investigations of the present inventors have shown that the characteristics of the chemical structure of the compounds of this invention consist in the fact that as is seen from general formula (I), a nitrogen atom at the 1-position of 1,2,3,4-tetrahydroquinoline which may be substituted by a chlorine atom is bonded to one nitrogen atom of imidazole through the carbonyl group. It has been found that when a chlorine atom is substituted at the 8-position of the tetrahydroquinoline in the above structure, there is a marked correlation between the herbicidal activity and the chemical structure of the compounds of the invention.

The compounds of general formula (III) which are intermediates for the production of the compounds of general formula (I) are also novel compounds not described in the literature known before the filing of the present application, and are useful as intermediates for the compounds of the invention represented by general formula (I).

It is an object of this invention to provide tetrahydroquinolin-1-ylcarbonylimidazole derivatives of general formula (I), intermediates thereof, processes for production thereof, and the use of these compounds as a herbicide or an agricultural or horticultural fungicide.

The above and other objects and advantages of this invention will become more apparent from the following description.

Since the compounds of this invention represented by general formula (I) are characterized by low toxicity to warm-blooded animals and good selectivity for cultivated plants, namely freedom from phytotoxicity to cultivated plants in usual dosage rates, they can be conveniently used, for example, as a herbicide for weed control. In particular, the herbicide of this invention shows an outstanding selective controlling effect when used as a preemergence soil treating agent or a stalk-leaf/soil treating agent against paddy weeds.

As stated above, the compounds of formula (I) have excellent safety, an outstanding herbicidal activity and a wide herbicidal spectrum.

For example, these compounds have significant herbicidal activity on the following paddy weeds without any injurious effect on rice plants:

| Plant's name | Latin nomenclature |
| --- | --- |
| Dicotyledons | |
| Kikashigusa | *Rotala indica* Koehne |

| Plant's name | Latin nomenclature |
| --- | --- |
| *-continued* | |
| False pimpernel | *Lindernia procumbens* Philcox |
| False loosestrife | *Ludwigia prostrata* Roxburgh |
| Largeleaf pondweed | *Potamogeton distinctus* A. Bennett |
| American waterwort | *Elatine triandra* Schk. |
| Monocotyledons | |
| Barnyard grass | *Echinochloa crus-galli* Beav. |
| Monochoria | *Monochoria vaginalis* Presl. |
| Spikerush | *Eleocharis acicularis* L. |
| Water chestnut | *Eleocharis kuroguwai* Ohwi |
| Umbrella plant | *Cyperus difformis* L. |
| Mizugayatsuri | *Cyperus serotinus* Rottboel |
| Urikawa | *Sagittaria pygmaea* Mig. |
| Narrowleaf water-plantain | *Alisma canaliculatum* A. Baun et Bouche |
| Bulrush | *Scirpus juncoides* Roxburgh var. |

Furthermore, these compounds of formula (I) have significant herbicidal activity on the following upland farm weeds:

| Plant's name | Latin nomenclature |
| --- | --- |
| Dicotyledons | |
| Tade | *Polygonum sp.* |
| Goosefoot | *Chenopodium album* linnaeus |
| Common chickweed | *Stellaria media* Villars |
| Common purslane | *Portulaca oleracea* Linnaeus |
| Monocotyledons | |
| Barnyard grass | *Echinochloa crus-galli* Beauv. var. |
| Fingergrass | *Digitaria adscendens* Henr. |
| Chufa | *Cyperus iria* L. |

The above-cited kinds of plants are typical examples of the genera given in Latin.

The applicability of the compounds of this invention represented by general formula (I) is not limited to paddy and upland farm weeds but they are also effective against hazardous weeds such as mat rush and weeds growing in lands temporarily out of cultivation. The weeds, as used herein, mean all plants which grow on undesired sites in the broadest sense.

The compounds of general formula (I) in accordance with this invention also show strong fungicidal activity on a broad range of fungi causing plant diseases and an excellent residual effect, and therefore can be applied to a control of plant diseases.

The fungicidal spectrum of these compounds shows that they can be effectively used to control plant diseases induced by Archimycetes, Phycomycetes, Ascomycetes, Basidiomycetes and Fungi Imperfecti and various bacteria.

Specifically, the compounds of this invention are useful for controlling, for example, brown spot of rice (*Ophiobolus miyabeanus*, black spot of cruciferous plants (*Alternaria brassicae*), alternaria leaf spot of apple (*Alternaria mali*), black spot of pear (*Alternaria kikuchina*), phytophthora blight of various crops (*Phytophthora infestans*), and anthracnose of oriental pickling melon (*Colletotrichum lagenarium*). Bacterial leaf spot of rice (*Xanthomonas oryzae*) which is an important bacterial disease can also be cited.

The compounds of general formula (I) in accordance with this invention can be easily produced, for example, by the following processes:

Process (i)

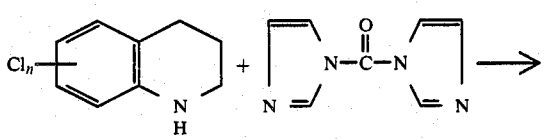

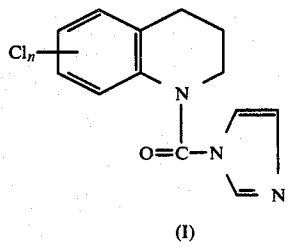
(I)

In the above scheme, n is as defined above.

Specific examples of the compound of general formula (II) used as a starting material in the process for producing the compounds of general formula (I) shown by the above reaction scheme include
1,2,3,4-tetrahydroquinoline,
6-chloro-1,2,3,4-tetrahydroquinoline,
8-chloro-1,2,3,4-tetrahydroquinoline,
5,7-dichloro-1,2,3,4-tetrahydroquinoline,
5,8-dichloro-1,2,3,4-tetrahydroquinoline,
6,8-dichloro-1,2,3,4-tetrahydroquinoline,
7,8-dichloro-1,2,3,4-tetrahydroquinoline,
5,6-dichloro-1,2,3,4-tetrahydroquinoline, and
5,6,8-trichloro-1,2,3,4-tetrahydroquinoline.

By citing the following typical example, the above process will be specifically described:

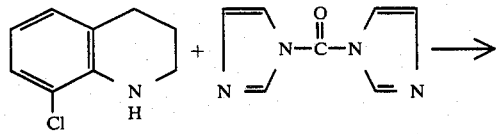

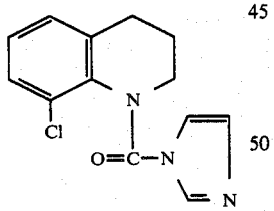

Desirably, the above process for producing the compound of this invention represented by general formula (I) can be carried out using a solvent or a diluent. For this purpose, all inert solvents and diluents can be used.

Examples of such solvents or diluents include water; aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, diisopropyl ether, dibutyl ether, propylene oxide, dioxane and tetrahydrofuran; ketones such as acetone, methyl ethyl ketone, methyl isopropyl ketone and ethyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide and dimethylacetamide; sulfones and sulfoxides such as dimethyl sulfoxide and sulfolane; and bases such as pyridine.

The above reaction may be carried out in the presence of an acid binder. Examples of the acid binder include the hydroxides, carbonates, bicarbonates and alcoholates of alkali metals and tertiary amines such as triethylamine, diethylaniline and pyridine, all of which are generally used.

The above process can be carried out over a wide temperature range. Generally, it can be carried out at a temperature between about −20° C. and the boiling point of the mixture, desirably between about 0° C. and about 100° C. Desirably, the reaction is carried out under normal atmospheric pressure, but it is also possible to operate under elevated or reduced pressures.

Process (ii)

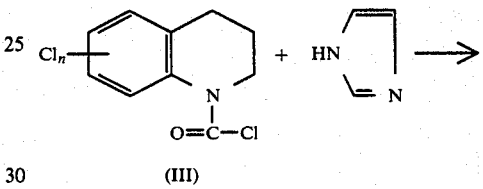
(III)

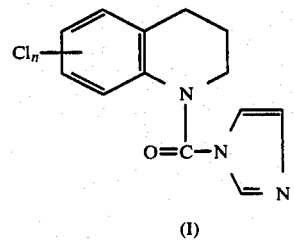
(I)

In the above reaction scheme, n is as defined hereinabove.

Specific examples of the compound of general formula (III) used as a starting material in the process for producing the compound of general formula (I) in accordance with this invention as shown by the above reaction scheme include
1(H),2,3,4-tetrahydroquinolin-1-ylcarbonyl chloride,
6-chloro-1(H),2,3,4-tetrahydroquinolin-1-ylcarbonyl chloride,
8-chloro-1(H),2,3,4-tetrahydroquinolin-1-ylcarbonyl chloride,
5,7-dichloro-1(H),2,3,4-tetrahydroquinolin-1-ylcarbonyl chloride,
5,8-dichloro-1(H),2,3,4-tetrahydroquinolin-1-ylcarbonyl chloride,
6,8-dichloro-1(H),2,3,4-tetrahydroquinolin-1-ylcarbonyl chloride,
7,8-dichloro-1(H),2,3,4-tetrahydroquinolin-1-ylcarbonyl chloride,
5,6-dichloro-1(H),2,3,4-tetrahydroquinolin-1-ylcarbonyl chloride, and
5,6,8-trichloro-1(H),2,3,4-tetrahyroquinolin-1-ylcarbonyl chloride.

By citing the following typical example, the above process will be specifically described

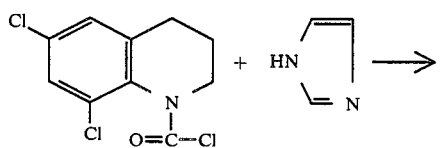

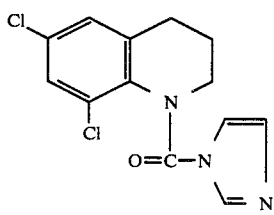

To carry out the above process, the same inert solvents or diluents as exemplified above are desirably used, and the desired product of high purity can be obtained in high yields.

The above process can be carried out over a broad temperature range, generally at a temperature between $-20°$ C. and the boiling point of the mixture, preferably between 0° and 100° C. The reaction is desirably carried out at atmospheric pressure, but it is also possible to operate under elevated or reduced pressures.

The compound of general formula (III) in accordance with this invention as an intermediate for the production of the compound of formula (I) can be produced, for example, by the following process (iii):

Process (iii)

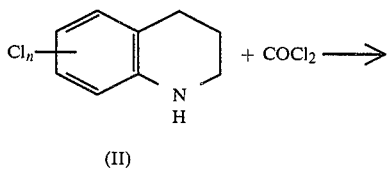

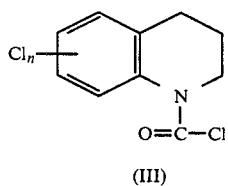

In the above reaction scheme, n is as defined hereinabove.

Specific examples of the compound of general formula (II) used as a starting material in the above process for producing the compound of general formula (III) in accordance with this invention as shown by the above reaction scheme may be the same as those exemplified for process (i) above.

As another starting material, trichloromethyl chloroformate (ClCOOCCl$_3$) can be reacted instead of phosgene.

To carry out the above process, the same inert solvents and diluents as exemplified above are desirably used, and the desired product of high purity can be obtained in high yields.

The above process can be carried out over a broad temperature range, generally at a temperature between $-20°$ C. and the boiling point of the mixture, preferably between 0° and 100° C. The reaction is carried out desirably at atmospheric pressure, but it is also possible to operate under elevated or reduced pressures.

As a herbicide or an agricultural and horticultural fungicide, the compounds of this invention may be used directly upon dilution with water, or in various formulations obtained by methods generally practiced in the production of agricultural chemicals using agriculturally acceptable adjuvants. In actual use, these various formulations may be applied directly or after diluting them with water to the desired concentrations.

The agriculturally acceptable adjuvants as referred to herein include, for example, diluents (solvents, extenders, carriers), surface-active agents (solubilizing agents, emulsifiers, dispersing agents, wetting agents), stabilizers, stickers, aerosol propellants and synergists.

Examples of the solvents are water, and organic solvents, for example hydrocarbons [such as n-hexane, petroleum ether, petroleum fractions (e.g., paraffin waxes, kerosene, light oils, middle oils and heavy oils), benzene, toluene, and xylene], halogenated hydrocarbons (such as methylene chloride, carbon tetrachloride, ethylene chloride, ethylene dibromide, chlorobenzene and chloroform), alcohols (such as methanol, ethanol, propanol and ethylene glycol), ethers (such as diethyl ether, ethylene oxide and dioxane), alcohol ethers (such as ethylene glycol monomethyl ether), ketones (such as acetone and isophorone), esters (such as ethyl acetate and amyl acetate), amides (such as dimethylformamide and dimethylacetamide) and sulfoxides (such as dimethyl sulfoxide).

Examples of the extenders or carriers include inorganic powders, for example slaked lime, magnesium lime, gypsum, calcium carbonate, silica, perlite, pumice, calcite, diatomaceous earth, amorphous silica, alumina, zeolites, and clay minerals (such as pyrophyllite, talc, montmorillonite, beidellite, vermiculite, kaolinite and mica); vegetable powders such as cereal flours, starches, processed starches, sugar, glucose and crushed stalks of plants; and powders of synthetic resins such as phenolic resins, urea resins, and vinyl chloride resins.

Example of the surface-active agents include anionic surface-active agents such as alkylsulfonic acid esters (such as sodium laurylsulfate), arylsulfonic acids (such as alkylarylsulfonoc acid salts and sodium alkylnaphthalenesulfonates), succinic acid salts, and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chloride) and polyoxyethylene alkylamines; nonionic surface-active agents such as polyoxyethylene glycol ethers (e.g., polyoxyethylene alkylaryl ethers and the condensation products thereof), polyoxyethylene glycol esters (e.g., polyoxyethylene fatty acid esters), and polyhydric alcohol esters (e.g., polyoxyethylene sorbitan monolaurate); and amphoteric surface-active agents.

Examples of other adjuvants include stabilizers; stickers (such as agricultural soaps, casein lime, sodium alginate, polyvinyl alcohol, vinyl acetate-type adhesives and acrylic adhesives); aerosol propellants (such as trichlorofluoromethane, dichlorofluoromethane, 1,2,2-trichloro-1,1,2-trifluoroethane, chlorobenzene, LNG, and lower ethers); combustion controlling agents for fumigants (such as nitrites, zinc powder, and dicyandiamide); oxygen-yielding agents (such as chlorates); effect-prolonging agents; dispersion stabilizers [such as casein, tragacanth, carboxymethyl cellulose (CMC), and polyvinyl alcohol (PVA)]; and synergists.

The compounds of this invention can be formulated into various forms by methods generally practiced in the production of agricultural chemicals. Illustrative of such forms are emulsifiable concentrates, oil preparations, wettable powders, soluble powders, suspensions, ducts, granules, pulverulent preparations, fumigants, tablets, aerosols, pastes and capsules.

The herbicide or agricultural and horticultural fungicide of this invention may contain about 0.001 to about 100% by weight, preferably about 0.005 to about 95% by weight, of the aforesaid active ingredient.

In actual use, the suitable amount of the active compound in the aforesaid various formulations and ready-to-use preparations is generally about 0.01 to about 95% by weight, preferably about 0.05 to about 60% by weight.

The content of the active ingredient can be properly varied depending upon the type of the formulation, the method, purpose, time and locus of its application, the state of occurrence of weeds and plant diseases.

If required, the compounds of this invention may be used in combination with other agricultural chemicals, for example insecticides, other fungicides, miticides, nematocides, antiviral agents, other herbicides, plant growth regulators and attractants [such as organophosphate compounds, carbamate compounds, dithio (or thiol) carbamate compounds, organochlorine compounds, dinitro compounds, organosulfur or organometallic compounds, antibiotics, substituted diphenyl ether compounds, urea compounds, and triazine compounds], and/or fertilizers.

Various formulations and ready-to-use preparations containing the aforesaid active ingredient of the invention can be applied by various methods generally practiced in the field of agricultural chemical application, for example spraying (liquid spraying, misting, atomizing, dusting, granule scattering, water surface application, pouring, etc.); fumigation; soil application (mixing, sprinkling, vaporing, pouring, etc.); surface application (coating, banding, dust coating, covering, etc.); and dipping. It can also be applied by the so-called ultralow volume spraying method. According to this method, the active ingredient may be included in an amount of 100%.

The rate of application of the active compound per unit area is, for example, about 0.5 to about 8 kg, preferably about 1 to about 5 kg, per hectare for the herbicide, and about 1 to about 10 kg per hectare for the agricultural and horticultural fungicide. In special cases, however, it may, and sometimes should, be outside the specified range.

According to this invention, there can be provided a herbicidal or an agricultural and horticultural fungicidal composition comprising the compound of general formula (I) as an active ingredient and a diluent (a solvent and/or an extender and/or a carrier) and/or a surface-active agent, and if further required, a stabilizer, a sticker, a synergist, etc.

This invention also provides a method for controlling weeds and plant diseases, which comprises applying to weeds, plant pathogens and/or the locus of their occurrence the compound of general formula (I) alone or in admixture with a diluent (a solvent and/or an extender and/or a carrier) and/or a surface-active agent and if further required, a stabilizer, a sticker, a synergist, etc.

The following examples illustrate the present invention more specifically. It should be noted however that the invention is not limited to these examples alone.

EXAMPLE 1

8-Chloro-1,2,3,4-tetrahydroquinoline (2.3 g) and N,N'-carbonyldiimidazole (1.8 g) were heated with stirring in toluene (20 ml) for 24 hours. The solvent was evaporated under reduced pressure, and the residue was concentrated at 80° C. and 1 mmHg. Water was added to the residue to crystallize it. The suspension was filtered to give the desired 8-chloro-1(H),2,3,4-tetrahydroquinolin-1-ylcarbonylimidazole (2.2 g) represented by the following formula as crystals. The product was recrystallized from ether. m.p. 122°–123° C.

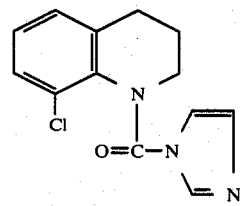

(Compound No. 1)

EXAMPLE 2

6,8-Dichloro-1(H),2,3,4-tetrahydroquinolin-1-yl-carbonyl chloride (2.63 g) and imidazole (2.0 g) were stirred in tetrahydrofuran (20 ml) at the refluxing temperature for 16 hours. Tetrahydrofuran and the excess of imidazole were evaporated under reduced pressure. Water was added to the residue to crystallize it. The suspension was filtered to give the desired 6,8-dichloro-1(H),2,3,4-tetrahydroquinolin-1-ylcarbonylimidazole (2.5 g) represented by the following formula as crystals. The product was recrystallized from ether. m.p. 137°–138° C.

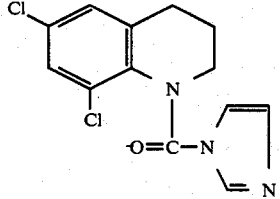

(Compound No. 2)

Table 1 below show compounds of general formula (I). in accordance with this invention which were synthesized by the same method as in Example 1 or 2.

TABLE 1

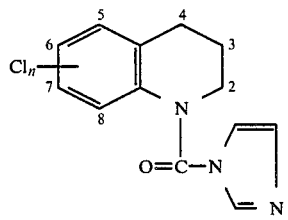

| Compound No. | Cl$_n$ | Physical constant |
|---|---|---|
| 3 | — | m.p. 97–98° C. |
| 4 | 6-Cl | m.p. 125–127° C. |
| 5 | 5,7-Cl$_2$ | m.p. 123–124° C. |
| 6 | 5,8-Cl$_2$ | m.p. 177–178° C. |
| 7 | 7,8-Cl$_2$ | m.p. 130–132° C. |
| 8 | 5,6,8-Cl$_3$ | m.p. 150–152° C. |

(Note):
In the table the mark "—" for compound No. 3 in the column of Cl$_n$ shows that it has no substituent.

EXAMPLE 3

Synthesis of an intermediate:

Trichloromethyl chloroformate (20 ml) was dissolved in ethyl acetate (100 ml), and the solution was warmed to 50° to 60° C. (oil bath temperature). With stirring, a solution of 6,8-dichloro-1,2,3,4-tetrahydroquinoline (10 g) in ethyl acetate (20 ml) was added over the course of 30 minutes. The reaction temperature was then gradually raised to the refluxing temperature, and stirred for 5 hours. The solvent was evaporated on a steam bath, and the residue was concentrated under reduced pressure to give the desired 6,8-dichloro-1(H),2,3,4-tetrahydroquinolin-1-ylcarbonyl chloride (10.5 g) represented by the following formula. The product was recrystallized from ether. m.p. 67°–68° C.

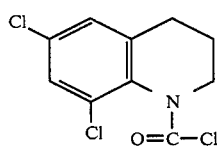

(Compound No. III-2)

Table 2 shows compounds of general formula (III) synthesized by the same method as in Example 3.

TABLE 2

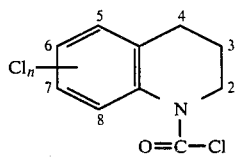

| Compound No. | Cl$_n$ | Physical constant |
|---|---|---|
| III-1 | 8-Cl | b.p. 143–145° C./0.5 mmHg |
| III-3 | — | b.p. 136–140° C./0.5 mmHg |
| III-4 | 6-Cl | b.p. 146–148° C./0.5 mmHg |
| III-5 | 5,7-Cl$_2$ | b.p. 168–170° C./0.5 mmHg |
| III-6 | 5,8-Cl$_2$ | m.p. 98–100° C. |
| III-7 | 7,8-Cl$_2$ | b.p. 165–167° C./0.3 mmHg |
| III-8 | 5,6,8-Cl$_3$ | b.p. 178–1809° C./0.5 mmHg |

(Note):
In the table, the mark "—" in the column of Cl$_n$ has the same meaning as in Table 1.

EXAMPLE 4

(wettable powder)

Fifteen parts of compound No. 1 of the invention, 80 parts of a 1:5 mixture of powdery diatomaceous earth and powdery clay, 2 parts of sodium alkylbenzenesulfonate, and 3 parts of a sodium alkylnaphthalenesulfonate/formaldehyde condensate are pulverized and mixed to form a wettable powder. It is diluted with water and sprayed onto weeds, pathogens and/or the the locus of their occurrence.

EXAMPLE 5

(emulsifiable concentrate)

Thirty parts of compound No. 2 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and sprayed onto weeds, pathogens and/or the locus of their occurrence.

EXAMPLE 6

(dust)

Two parts of compound No. 3 of the invention and 98 parts of powdery clay are pulverized and mixed to form a dust. It is scattered over weeds, pathogens and/or the locus of their occurrence.

EXAMPLE 7

(dust)

Compound No. 2 of the invention (1.5 partgs), 0.5 part of isopropyl hydrogen phosphate (PAP) and 98 parts of powdery clay are pulverized and mixed to form a dust. It is scattered over weeds, pathogens and/or the locus of their occurrence.

EXAMPLE 8

(granules)

Water (25 parts) is added to a mixture consisting of 10 parts of compound No.1 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over weeds, pathogens and-/or the locus of their occurrence.

EXAMPLE 9

(granules)

Ninety-five parts of clay mineral particles having a particle size distribution between 0.2 and 2 mm are put in a rotary mixer, and with rotation, 5 parts of compound No. 2 of the invention dissolved in an organic solvent is sprayed onto the particles to wet them uniformly to form granules. The granules are scattered over weeds, pathogens and/or the locus of their occurrence.

EXAMPLE 10

(biological test)

Test of stalk-leaf/soil treatment of paddy weeds in the flooded state (pot test):

Preparation of an active compound

Carrier: 5 parts by weight of acetone

Emulsifier: 1 part by weight of benzyloxypolyglycol ether

A preparation containing the active compound is formed by mixing 1 part by weight of each of the active compounds with the carrier and emulsifier in the amounts indicated above, and diluting a predetermined amount of the resulting emulsifiable concentrate with water.

Testing procedure

Aquatic paddy soil was filled in Wagner pots (1/5,000 ares), and rice seedlings (variety: Kinmaze) in the 2- to 3-leaf stage (plant height about 10 cm) were transplanted at a rate of 2 per pot. Seeds of *Echinochloa crus-galli, Cyperus microiria, Monochoria vaginalis, Scirpus juncoides* and broad-leaved weeds, small fragments of *Eleocharis acicularis*, and tubers of *Cyperus serotinus* and *Sagittaria pygmaea* were inoculated in the pots. The soil in the pots was maintained in the wet state. After *Echinochloa crus-galli* grew to a stage of approximately two leaves (about 7 to 9 days after inoculation), each pot was watered to a depth of about 6 cm. A predetermined amount of the compound of this invention in the form of an emulsion was applied by means of a pipette to treat each pot. After the treatment, the pots were subjected to a water leaking treatment for 2 days at a rate of 2 to 3 cm per day, and thereafter maintained in the watered state to a depth of about 3 cm. In the fourth week after the treatment with the chemical, the herbicidal effect and the degree of phytotoxicity were rated on a scale of 0 to 5 as follows:

Evaluation of the herbicidal effect (herbicidal rate based on the non-treated area):

5: at least 95% (withered)
4: at least 80% but less than 95%
3: at least 50% but less than 80%
2: at least 30% but less than 50%
1: at least 10% but less than 30
0: less than 10% (no effect)

Evaluation of phytotoxicity to aquatic rice plants (the phytotoxicity rate based on the non-treated area):

5: at least 90% (fatal injury)
4: at least 50% but less than 90%
3: at least 30% but less than 50%
2: at least 10% but less than 30%
1: more than 0% but less than 10%
0: 0% (no phytotoxicity)

The test results are shown in Table 3.

The weeds are shown by the following abbreviations A, B, C, D, E, F, G and H.

A: *Echinochloa crus-galli*
B: *Eleocharis acicularis*
C: *Cyperus microiria*
D: *Scirpus juncoides*
E: *Monochoria vaginalis*
F: Broad-leaved weeds (*Lindernia procumbens, Rotala indica, Elatine triandra*, etc.)
G: *cyperus serotinus*
H: *Sagittaria pygmaea*

TABLE 3

| Compound No. | Amount of the active component (kg/ha) | Herbicidal effect Weed | | | | | | | | Phytotoxicity Rice |
|---|---|---|---|---|---|---|---|---|---|---|
| | | A | B | C | D | E | F | G | H | |
| 1 | 20 | 5 | 5 | 5 | 5 | 5 | 5 | 5 | 5 | 0 |
| 2 | 20 | 5 | 5 | 5 | 5 | 5 | 5 | 5 | 5 | 0 |
| 6 | 20 | 5 | 5 | 5 | 5 | 5 | 5 | 5 | 5 | 0 |
| 7 | 20 | 5 | 5 | 5 | 5 | 5 | 5 | 5 | 5 | 0 |
| 8 | 20 | 5 | 5 | 5 | 5 | 5 | 5 | 5 | 5 | 0 |
| Control | | | | | | | | | | |
| A-1 | 20 | 0 | 0 | 1 | 0 | 0 | 1 | 0 | 0 | 0 |
| B-1 | 20 | 0 | 0 | 1 | 0 | 1 | 2 | 0 | 0 | 0 |

Note
Control A-1: the compound described in the above-cited U.S. Pat. No. 3,308,131.

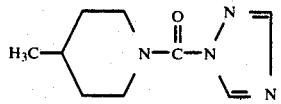

Control B-1: the compound described in the above-cited Japanese Patent Publication No. 17748/1968

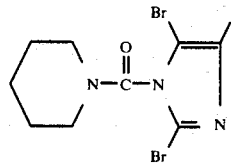

EXAMPLE 11

(biological test)

Test for efficacy on *Cochliobolus miyabeanus* by stalk-/leave spraying:

Rice plants (variety: kusabue) were cultivated in unglazed pots having a diameter of 12 cm, and in the 3- to 4-leaf stages, a dilution of the test compound prepared in accordance with Example 4 was sprayed at a rate of 50 ml per three pots. On the next day, a suspension of artificially cultivated spores of *Cochliobolus miyabeanus* was sprayed twice onto the pots. The pots were maintained in a humid chamber having a relative humidity of 100% and a temperature of 25° C. to induce infection. Seven days after the inoculation, the degree of disease per pot was rated on a scale of 0 to 5 as follows, and the control index (%) was calculated.

| Degree of disease | Extent of disease |
|---|---|
| 0 | No disease |
| 1 | Slight |
| 2 | Small |
| 3 | Medium |
| 4 | Great |
| 5 | Very great |

Control index (%) = $\dfrac{\text{Degree of disease in the non-treated area} - \text{Degree of disease in the treated area}}{\text{Degree of disease in the non-treated area}} \times 100$ In this test, three pots constituted one lot. Compounds Nos. 1, 2 and 4 showed a control index of 100% when the concentration of the active component was 500 ppm. The control compounds A-1 and B-1 in Example 9 showed a control value of less than 10% when the concentration of the active component was 500 ppm.

EXAMPLE 12

(biological test)

Test for control of late blight of tomato (*Phytophthora infestans*)

Each of the test compounds in the form of an emulsion prepared in accordance with Example 4 was sprayed by a spray gun on tomato (variety: Kurihara) grown in 9 cm unglazed pots. One day later, a suspension of spores of the present pathogen was inoculated and the pots were left to stand overnight in a constant temperature chamber kept at a temperature of 22° C. and a humidity of at least 90%. Five days later, the degree of disease was rated on the following standards by the percentage of the area of lesions, and the control index was calculated.

| Degree of disease | Percentage of the area of lesions (%) |
|---|---|
| 0 | 0 |
| 0.5 | 2 or less |
| 1 | 3-5 |
| 2 | 6-15 |
| 3 | 16-30 |
| 4 | 31-50 |
| 5 | 51 or more |

$$\text{Control index (\%)} = \frac{\text{Degree of disease in the non-treated area} - \text{Degree of disease in the treated area}}{\text{Degree of disease in the non-treated area}} \times 100$$

Compound No. 3 showed a control effect of 100% when the concentration of the active component was 500 ppm. The control compounds A-1 and B-1 showed a control value of 0%.

EXAMPLE 13

(biological test)

Test for controlling *Alternaria brassicae* on cruciferous vegetable:

A chemical in a predetermined concentration prepared as in Example 11 was sprayed at a rate of 25 ml per three pots onto small seedlings of Chinese cabbage grown in 9 cm vinyl plastic pots after seeding. On the day next to the day of spraying, a suspension of conidiospores of the present pathogen obtained by cultivation in a potato-agar medium was inoculated in the treated Chinese cabbage by spraying, and the pots were maintained for one day in a humid chamber (relative humidity 100%) at 25° C. Then, they were transferred to a glass greenhouse (20°-30° C.) for infection. Seven days after the inoculation, the degree of disease per pot was rated on the same scale as in Example 10, and the control index was calculated. It was found that, for example, compound No. 4 showed a control index of 100% at an active ingredient concentration of 500 ppm, whereas control compounds A-1 and B-1 showed a control of 0 at 500 ppm.

EXAMPLE 14

(biological test)

Control test on *Alternaria mali* of apple:

A solution in a predetermined concentration of each of the test compounds was sprayed at a rate of 100 ml per three pots onto young seedlings of apple (variety: star king, biennial seedlings) grown in #3 unglazed pots and having about 10 newly developed leaves.

On the day next to the day of spraying, a suspension of conidiospores of *Alternaria mali* (cultivated for 7 days in an apricot medium) was inoculated on the treated apple seedings by spraying, and the pots were maintained for 2 days in a humid chamber at 25° C.

Three days after the inoculation, the number of lesions was examined with respect to ten leaves in each of the pots, and the average umber of lesions per leaf was calculated. The control index was calculated in accordance with the following equation.

$$\text{Control index (\%)} = \frac{\text{Average number of lesions of the non-sprayed area} - \text{Average number of lesions in the treated area}}{\text{Average number of lesions in the non-sprayed area}} \times 100$$

It was found that compound No. 4 showed a control index of 100% at an active ingredient concentration of 500 ppm, whereas control compounds A-1 and B-1 showed a control index of 0 at 500 ppm.

It will be appreciated that the instant specification and examples are set forth by way of illustration and not limitation, and that various modifications and changes may be made without departing from the spirit and scope of the present invention.

What is claimed is:

1. A tetrahydroquinolin-1-ylcarbonylimidazole of the formula

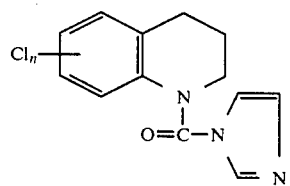

in which n is 0, 1, 2 or 3.

2. A compound according to claim 1, wherein such compound is 1-[-chloro-1(H),2,3,4-tetrahydroquinolin-1-yl-carbonyl]imidazole of the formula

3. A compound according to claim 1, wherein such compound is 1-[6,8-dichloro-1(H),2,3,4-tetrahydroquinolin-1-yl-carbonyl]imidazole of the formula

4. A herbicidal composition comprising a herbicidally effective amount of a tetrahydroquinolin-1-ylcarbonylimidazole according to claim 1 in admixture with a diluent.

5. A method of combating unwanted vegetation which comprises applying thereto or to a locus from which it is desired to exclude such vegetation a herbicidally effective amount of a tetrahydroquinolin-1-ylcarbonylimidazole according to claim 1.

6. The method according to claim 5, wherein such compound is 1-[8-chloro-1(H),2,3,4-tetrahydroquinolin-1-yl-carbonyl]imidazole.

7. The method according to claim 5, wherein such compound is 1-[6,8-dichloro-1(H),2,3,4-tetrahydroquinolin-1-yl-carbonyl]imidazole.

* * * * *